(12) United States Patent
Birchall, Jr. et al.

(10) Patent No.: US 6,572,623 B1
(45) Date of Patent: Jun. 3, 2003

(54) METHOD AND APPARATUS FOR ATTACHING A CRANIAL FLAP

(75) Inventors: Charles Fredrick Birchall, Jr., Mentor, OH (US); James Michael Kuras, Macedonia, OH (US)

(73) Assignee: Medtronic PS Medical, Inc., Goleta, CA (US)

( * ) Notice: Subject to any disclaimer, the term of this patent is extended or adjusted under 35 U.S.C. 154(b) by 126 days.

(21) Appl. No.: 09/625,473

(22) Filed: Jul. 25, 2000

(51) Int. Cl.⁷ .............................................. A61B 17/56
(52) U.S. Cl. .......................................... 606/76; 606/72
(58) Field of Search .............................. 606/76, 72, 77, 606/78

(56) References Cited

U.S. PATENT DOCUMENTS

| | | | |
|---|---|---|---|
| 4,468,201 A | * 8/1984 | Fukuyo | 433/176 |
| 4,612,923 A | 9/1986 | Kronenthal | 606/77 |
| 4,968,317 A | 11/1990 | Törmälä et al. | 606/77 |
| 4,976,715 A | 12/1990 | Bays et al. | 606/77 |
| 5,290,281 A | * 3/1994 | Tschakaloff | 606/77 |
| 5,549,620 A | * 8/1996 | Bremer | 606/72 |
| 5,569,250 A | 10/1996 | Sarver et al. | 606/69 |
| 5,769,899 A | 6/1998 | Schwartz et al. | 623/18 |
| 5,868,746 A | 2/1999 | Sarver et al. | 606/69 |
| 6,022,351 A | 2/2000 | Bremer et al. | 606/72 |
| 6,126,663 A | * 10/2000 | Hair | 606/72 |
| 6,197,037 B1 | * 3/2001 | Hair | 600/72 |

OTHER PUBLICATIONS

An article entitled Synthetic Biodegradable Polymers as Medical Devices, by John C. Middleton et al., published in Mar. 1998 in Medical Plastics and Biomaterials Magazine.

* cited by examiner

Primary Examiner—John J. Wilson
(74) Attorney, Agent, or Firm—Tarolli, Sundheim, Covell & Tummino L.L.P.

(57) ABSTRACT

A method and apparatus are provided for attaching a cranial flap (20) to a skull (10). The cranial flap (20) and the skull (10) are spaced apart by a kerf (22) defined by a first kerf edge (24) on the cranial flap and a second kerf edge (28) on the skull. The apparatus comprises at least one attachment device (30) made of a bioabsorbable polymeric material and having a head portion (40), a main body portion (32), and an end portion (50). The end portion (50) is deformable from an axially extending first condition to a radially extending second condition by heating the end portion and forming the end portion around the first kerf edge (24), which clamps the attachment device (30) to the cranial flap (20). The main body portion (32) includes a first surface portion (36) that attaches to the first kerf edge (24) and a second surface portion (38) that attaches to the second kerf edge (28). The attachment device (30) is positionable in the kerf (22) to secure the cranial flap to the skull by frictional engagement between the first surface portion (36) against the first kerf edge (24) and frictional engagement between the second surface portion (38) against the second kerf edge (28).

17 Claims, 2 Drawing Sheets

METHOD AND APPARATUS FOR ATTACHING A CRANIAL FLAP

FIELD OF THE INVENTION

The present invention is directed to a method and apparatus for attaching a cranial flap to a skull, from which the cranial flap was removed, during surgery.

BACKGROUND OF THE INVENTION

Surgical operations involving the human skull, such as brain surgery or craniofacial surgery, require that a section of the skull be removed. Typically, a number of burr holes are first drilled into the skull and which outline the section of the skull to be removed. A cutting tool is then inserted into one of the burr holes and a cut, or osteotomy, is made from one burr hole to then next burr hole until a loop is completed. The loop of osteotomies forms an opening in the skull and defines the section of the skull to be removed. The section of the skull to be removed is commonly referred to as a cranial flap. Because the blade on the cutting tool typically has a width of 1–2 mm, a kerf is formed between the opening in the skull and the cranial flap. Thus, the periphery of the cranial flap is smaller than the opening in the skull.

When the surgical procedure inside the skull is complete, the cranial flap must be replaced in the opening in the skull and re-attached to the skull. A number of methods are known for re-attaching the cranial flap to the skull. One known method uses stainless steel wire as a suture material. Other known methods utilize plates and associated screws made from either titanium or a bioabsorbable polymer. Still other known methods employ rivet-type fasteners made of titanium or a biocompatible polymer such as acetyl resin.

A major disadvantage of the known methods for reattaching a cranial flap that use a metallic material is that the metal creates large artifacts in any subsequent CT scans and radiographs. It is also disadvantageous to use a permanent (non-bioabsorbable) fastener that protrudes more than 1–2 mm from the surface of the skull because the fasteners then become visible as unsightly bumps under the patient's skin.

SUMMARY OF THE INVENTION

The present invention is an apparatus for attaching a cranial flap to a skull during surgery. The cranial flap and the skull are spaced apart by a kerf defined by a first kerf edge on the cranial flap and a second kerf edge on the skull. The apparatus comprises at least one attachment device made of a bioabsorbable polymeric material. The at least one attachment device has a head portion, a main body portion, and an end portion that is deformable upon heating to a predetermined temperature. The end portion of the at least one attachment device has a first condition in which the end portion extends axially from the main body portion and a second condition in which the end portion extends radially from the main body portion and engages an inner surface of the cranial flap. The end portion is deformable from the first condition to the second condition during surgery by heating the end portion and forming the end portion around the first kerf edge of the cranial flap to clamp the at least one attachment device to the cranial flap. The main body portion of the at least one attachment device includes a first surface portion that attaches to the first kerf edge on the cranial flap and a second surface portion that attaches to the second kerf edge on the skull. The at least one attachment device is positionable in the kerf between the cranial flap and the skull to secure the cranial flap to the skull by frictional engagement between the first surface portion against the first kerf edge and frictional engagement between the second surface portion against the second kerf edge.

The present invention also provides a method for re-attaching a cranial flap to a skull during surgery. The method utilizes an attachment device made of a bioabsorbable material that is formable upon heating to a predetermined temperature. The attachment device has a head portion, a main body portion, and a deformable end portion extending axially from the main body portion. The attachment device is placed adjacent the cranial flap so that the head portion engages an outer surface of the cranial flap and the main body portion engages a first kerf edge of the cranial flap. The end portion of the attachment device is heated to a predetermined temperature and subsequently bent around the cranial flap so that the end portion extends radially and engages an inner surface of the cranial flap. The cranial flap is then pressed into an opening in the skull created by the removal of the cranial flap so that frictional engagement between the main body portion of the attachment device and the cranial flap and frictional engagement between the main body portion of the attachment device secures the cranial flap to the skull.

BRIEF DESCRIPTION OF THE DRAWINGS

The foregoing and other features of the present invention will become apparent to those skilled in the art to which the present invention relates upon reading the following description with reference to the accompanying drawings, in which.

DESCRIPTION OF PREFERRED EMBODIMENTS

The present invention is directed to a method and apparatus for attaching a cranial flap to a skull, from which the cranial flap was removed, during surgery. As representative of the present invention, FIG. 1 illustrates a human skull 10 on which surgery is being performed.

Figure 1:
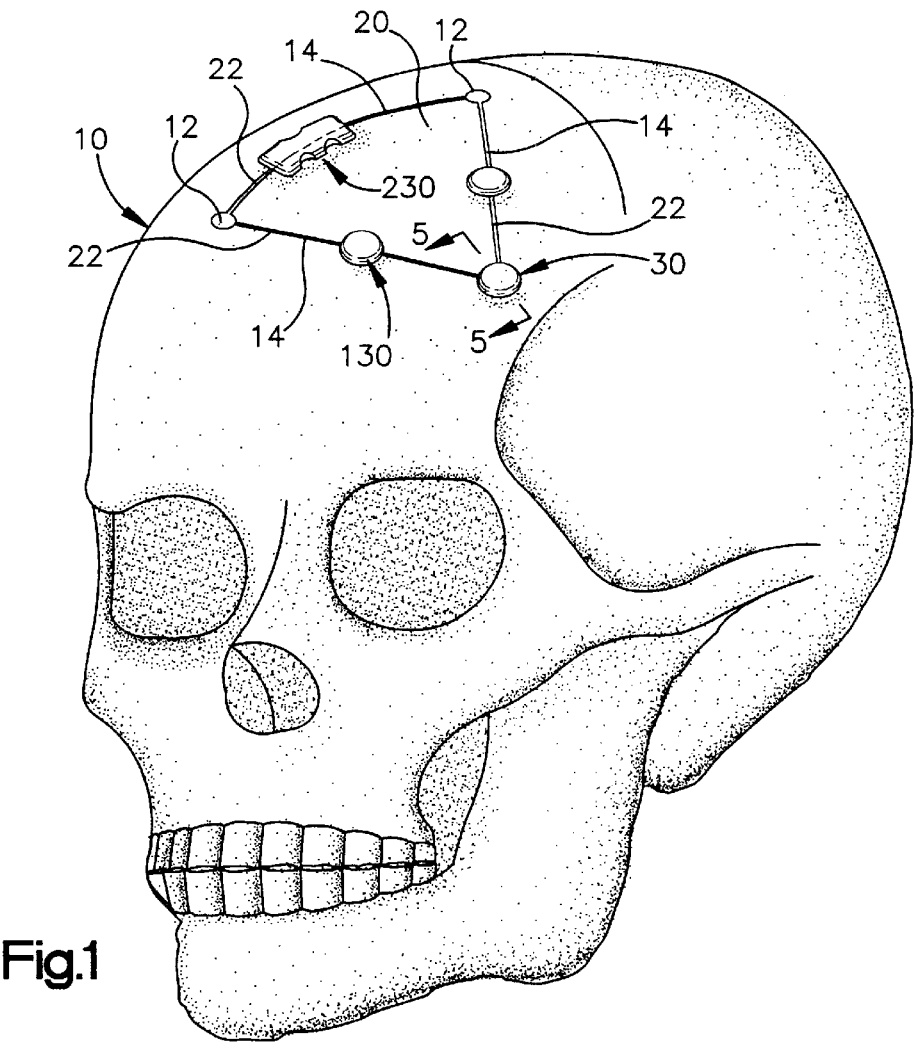
FIG. 1 is a perspective view of a human skull illustrating several apparatuses for attaching a cranial flap in accordance with multiple embodiments of the present invention.

To access a particular region inside the skull 10, the surgeon drills a number of burr holes 12, only two of which are visible in FIG. 1, in the skull. A cutting tool (not shown) is then inserted into a first one of the burr holes 12 and a cut 14 is made in the skull 10 from the first one of the burr holes to another of the burr holes. Additional cuts 14 in the skull 10 are made between the other burr holes 12 until a loop is completed. In the representative illustration of FIG. 1, there are three cuts 14. It should be apparent that more than three burr holes 12 and three cuts 14 may be made at the discretion of the surgeon.

The loop of cuts 14 in the skull 10 forms an opening (not numbered) in the skull and defines a cranial flap 20 to be removed. While making the cuts 14, the width of the cutting tool forms a kerf 22 between the cranial flap 20 and the skull 10. Hence, the cranial flap 20 is slightly smaller than the opening in the skull 10. When the surgical procedure inside the skull 10 is complete, the cranial flap 20 is replaced in the opening in the skull and secured to the skull according to the method and apparatus described below.

Figure 2:
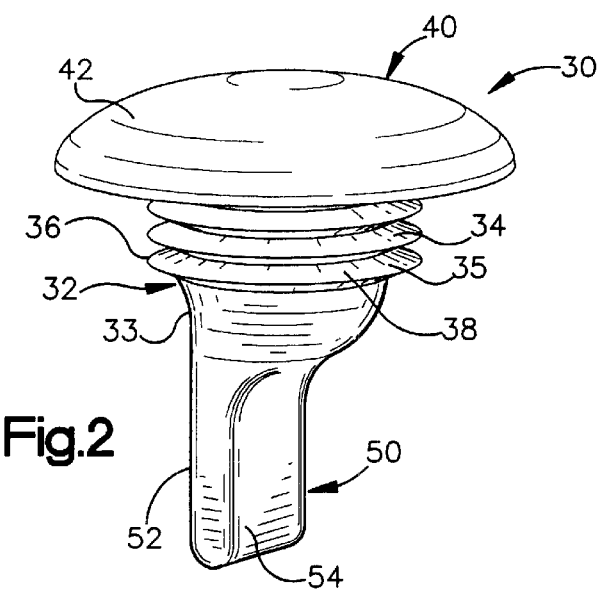
FIG. 2 is a perspective view of an apparatus for attaching a cranial flap in accordance with a first embodiment of the present invention.

A first embodiment of an attachment device 30 for securing the cranial flap 20 to the skull 10 is illustrated in FIG. 2. The attachment device 30 according to the first embodiment is designed to fit into one of the burr holes 12 in the skull 10, as is described further below. The attachment device 30 is made of a bioabsorbable polymeric material, such as polylactide (PLA), polyglycolide (PGA), or a co-polymer of polylactide and polyglycolide. The attachment device 30 has a main body portion 32, a head portion 40, and a deformable end portion 50.

The main body portion 32 of the attachment device 30 has a generally cylindrical outer surface 33. An upper section 34 of the outer surface 33 has a plurality of circumferentially extending teeth 35. The teeth 35 extend through diametrically opposed first and second surface portions 36 and 38 in the upper section 34 of the outer surface 33. In accordance with the embodiment of FIG. 2, the first and second surface portions 36 and 38 comprise arcuate segments. Further, the main body portion 32 preferably has an axial length L1 that is between 3 mm and 5 mm to allow the attachment device 30 to adapt to various skull thicknesses.

Figure 3:
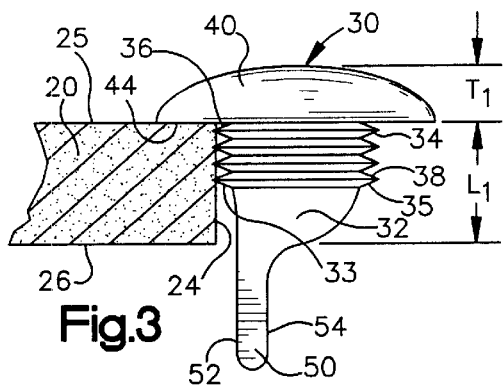
FIG. 3 is a sectional view of the apparatus of FIG. 2 at an early stage in the attachment process.

The head portion 40 of the attachment device 30 has a domed outwardly facing surface 42 and a planar inwardly facing surface 44 (FIG. 3). The head portion 40 preferably has an axial thickness T1 of no more than 2 mm to reduce the visibility of the head portion while the attachment device 30 is being absorbed.

The end portion 50 of the attachment device 30 includes generally parallel first and second side surfaces 52 and 54. The end portion 50 has a first condition in which the end portion extends axially from the main body portion 32. The end portion 50 further has a second condition, illustrated in FIG. 4, in which the end portion extends generally radially from the main body portion 32, and the first side surface 52 faces in an upward (as viewed in the Figures) direction A. The end portion 50 of the attachment device 30 is deformable from the first condition to the second condition by heating the end portion.

To re-attach the cranial flap 20 to the skull 10, at least one attachment device 30 is first secured to the cranial flap. As shown in FIG. 3, the attachment device 30 is placed next to the cranial flap 20 so that the teeth 35 on the first surface portion 36 of the main body portion 32 of the attachment device engage a first kerf edge 24 on the cranial flap. Further, the inwardly facing surface 44 on the head portion 40 of the attachment device 30 is brought into engagement with an outer surface 25 of the cranial flap. The attachment device 30 is positioned so that the first side surface 52 on the end portion 50 lies underneath and generally parallel to the first kerf edge 24 on the cranial flap 20.

In accordance with the first embodiment of the invention, the cylindrical main body portion 32 of the attachment device 30 fits into one of the burr holes 12 in the skull 10.

The first kerf edge 24 has an arcuate shape formed by the drill bit (not shown) used to create the burr hole, and the first surface portion 36 on the main body portion 32 of the attachment device 30 adjoins this arcuate first kerf edge.

Figure 4:
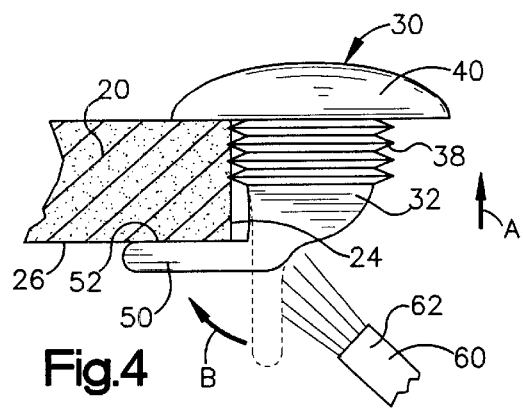
FIG. 4 is a view similar to FIG. 3 illustrating a subsequent stage in the attachment process.

Next, the end portion 50 of the attachment device 30 is heated to a predetermined elevated temperature by a suitable heat source such as a heat gun 60, an exhaust nozzle 62 of which is illustrated schematically in FIG. 4. The predetermined elevated temperature to which the end portion 50 is heated will depend on the glass transition temperature of the specific bioabsorbable polymeric material of the attachment device 30, but will likely be in the range of 50–100° C.

Upon being heated to the predetermined elevated temperature, the end portion 50 of the attachment device 30 is deformed into the second condition illustrated in FIG. 4 by bending the end portion around the first kerf edge 24 of the cranial flap 20 in the direction of arrow B. The end portion 50 of the attachment device 10 is bent in the direction of arrow B until the first side surface 52 on the end portion engages an inside surface 26 on the cranial flap 20. As the end portion 50 of the attachment device 30 cools and re-hardens in the position shown in FIG. 4, the attachment device becomes clamped to the cranial flap 20. Cooling of the end portion 50 may be accelerated using a fan (not shown) or other suitable device.

In order to use the attachment device 30 for attaching the cranial flap to the skull, additional attachment devices should be secured around the periphery of the cranial flap 20. It should be understood that it is not necessary that one or more attachment devices be located to fit in a burr hole 12. The number and location of additional attachment devices to be used are decisions made by the surgeon either before or during surgery. The surgeon may use several of the attachment devices 30 according to the first embodiment of FIGS. 2–5 or, alternatively, may utilize additional attachment devices constructed in accordance with either the second embodiment (FIG. 6) or the third embodiment (FIGS. 7 and 8) of the present invention.

Figure 6:
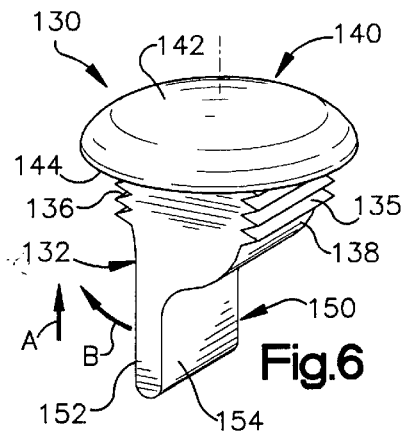
FIG. 6 is a perspective view of an apparatus for attaching a cranial flap in accordance with a second embodiment of the present invention.

An attachment device 130 constructed in accordance with the second embodiment of the invention is illustrated in FIG. 6. As is best seen in FIG. 1, the attachment device 130 is designed to fit into the kerf 22 that extends between two of the burr holes 12 in the skull 10. As with the first embodiment, the attachment device 130 is made of a bioabsorbable polymeric material, such as polylactide (PLA), polyglycolide (PGA), or a co-polymer of polylactide and polyglycolide. The attachment device 130 (FIG. 6) has a main body portion 132, a head portion 140, and a deformable end portion 150.

The main body portion 132 of the attachment device 130 has a generally square shape including diametrically opposed first and second surface portions 136 and 138. Further, the main body portion 132 has an axial length that is between 3 mm and 5 mm to allow the attachment device 130 to adapt to various skull thicknesses.

The head portion 140 of the attachment device 130 has a domed outwardly facing surface 142 and a planar inwardly facing surface 144 for engaging the outer surface 25 of the cranial flap 20. Like the attachment device 30 of FIG. 3, the head portion 140 preferably has an axial thickness of no more than 2 mm to reduce the visibility of the head portion while the attachment device is being absorbed into the skull.

The end portion 150 of the attachment device 130 includes generally parallel first and second side surfaces 152 and 154. The end portion 150 has a first condition in which the end portion extends axially from the main body portion 132. The end portion further has a second condition in which the end portion 150 extends generally radially from the main body portion 132 and the first side surface 152 faces upward. The end portion 150 of the attachment device 130 is deformable from the first condition to the second condition by heating the end portion to a predetermined elevated temperature.

The attachment device 130 is secured to the cranial flap 20 in same manner as the attachment device 10 of the first embodiment and therefore is not separately illustrated. The attachment device 130 is placed next to the cranial flap 20 so that the teeth 135 on the first surface portion 136 of the main body portion 132 of the attachment device engage the first kerf edge 24. The inwardly facing surface on the head portion 140 of the attachment device 150 is brought into engagement with the outer surface 25 of the cranial flap 20. The attachment device 130 is positioned so that the first side surface 152 on the end portion 150 lies underneath and generally parallel to the first kerf edge 24 on the cranial flap 20.

The end portion 150 of the attachment device 130 is then heated to a predetermined elevated temperature by a suitable heat source, such as the heat gun 60 shown schematically in FIG. 4. Upon being heated to the predetermined elevated temperature, the end portion 150 of the attachment device 130 is deformed into the second condition by bending the end portion around the first kerf edge 25 of the cranial flap 20 in the direction of arrow B. The end portion 150 of the attachment device 130 is bent in the direction of arrow B until the first side surface 152 on the end portion engages the inside surface 26 on the cranial flap 20. As the end portion 150 of the attachment device 130 cools and hardens, the attachment device becomes clamped to the cranial flap 20. Cooling of the end portion 150 may be accelerated using a fan (not shown) or other suitable device.

Figure 7:
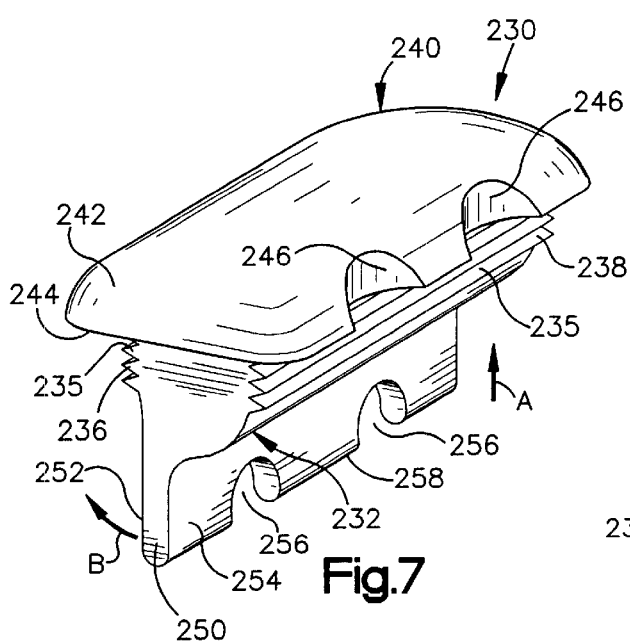
FIG. 7 is a perspective view of an apparatus for attaching a cranial flap in accordance with a third embodiment of the present invention.
Figure 8:
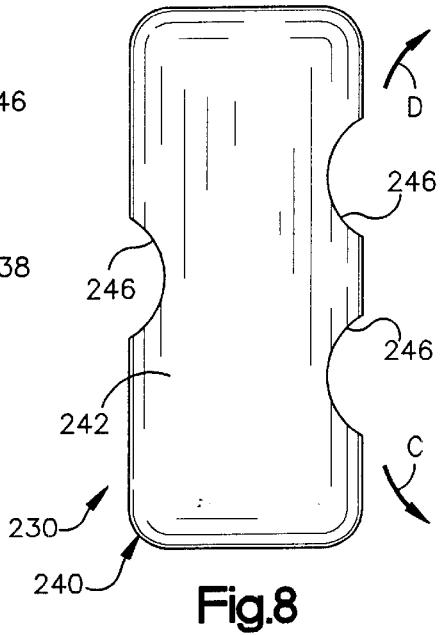
FIG. 8 is a plan view of the apparatus of FIG. 7.

An attachment device 230 constructed in accordance with the third embodiment of the invention is illustrated in FIGS. 7 and 8. As is best seen in FIG. 1, the attachment device 230 is designed to fit into the kerf 22 that extends between two of the burr holes 12 in the skull 10. As with the first embodiment, the attachment device 230 is made of a bioabsorbable polymeric material, such as polylactide (PLA), polyglycolide (PGA), or a co-polymer of polylactide and polyglycolide. The attachment device 230 (FIG. 7) has a main body portion 232, a head portion 240, and a deformable end portion 250. The attachment device 230 is basically an elongated version of the attachment device 130 of FIG. 6, but with a few additional features.

The head portion 240 of the attachment device 230 has a domed outwardly facing surface and a planar inwardly facing surface 244. As shown in FIGS. 7 and 8, the head portion 240 further includes a plurality of relief slots 246 located along the periphery of the head portion. The relief slots 246 make it easier for the head portion 240 to bend laterally, as is indicated by arrows C and D in FIG. 8, so that the attachment device 230 can adapt to a curved section of the kerf 22. The head portion 240 preferably has an axial thickness of no more than 2 mm to reduce the visibility of the head portion while the attachment device 230 is being absorbed.

The main body portion 232 of the attachment device 230 has a generally rectangular shape including diametrically opposed first and second surface portions 236 and 238 having teeth 235. Further, the main body portion 232 preferably has an axial length that is between 3 mm and 5 mm to allow the attachment device 230 to adapt to various skull thicknesses.

The end portion 250 of the attachment device 230 includes generally parallel first and second side surfaces 252 and 254. The end portion 250 further includes a plurality of relief notches 256 located along a bottom edge 258 of the end portion. The relief notches 256 make it easier for the end portion 250 to bend laterally as indicated by arrows C and D, so that the attachment device 230 can adapt to a curved section of the first kerf edge 24 on the cranial flap 20.

As with the previous embodiments, the end portion 250 has a first condition in which the end portion extends axially from the main body portion 232. The end portion 250 further has a second condition in which the end portion extends generally radially from the main body portion 232 and the first side surface 252 faces upward. The end portion 250 of the attachment device 230 is deformable from the first condition to the second condition by heating the end portion to a predetermined elevated temperature.

The attachment device 230 is secured to the cranial flap 20 in same manner as the attachment device 30 of the first embodiment and therefore is not separately illustrated. The attachment device 230 is placed next to the cranial flap 20 so that the teeth 235 on the first surface portion 234 of the main body portion 232 of the attachment device engage the first kerf edge 24. The inwardly facing surface 244 on the head portion 240 of the attachment device 230 is brought into engagement with the outer surface 25 of the cranial flap 20. The attachment device 230 is positioned so that the first side surface 252 on the end portion 250 lies underneath and generally parallel to the first kerf edge 24 on the cranial flap 20.

Next, the end portion 250 of the attachment device 230 is heated to a predetermined elevated temperature by a suitable heat source, such as the heat gun 60 shown schematically in FIG. 4. Upon being heated to the predetermined elevated temperature, the end portion 250 of the attachment device 230 is deformed into the second condition by bending the end portion around the first kerf edge 24 of the cranial flap 20 in the direction of arrow B. The end portion 230 of the attachment device 250 is bent in the direction of arrow B until the first side surface 252 on the end portion engages the inside surface 26 on the cranial flap 20. As the end portion 250 of the attachment device 230 cools and hardens, the attachment device becomes clamped to the cranial flap 20. Cooling of the end portion 250 may be accelerated using a fan (not shown) or other suitable device.

With a suitable number of attachment devices 30, 130 and/or 230 secured to the cranial flap 20, the cranial flap is then placed into the opening in the skull 10 in the same orientation as the cranial flap was removed from the opening. For the sake of clarity, only the attachment device 30 is further described, but it should be understood that the attachment devices 130 and 230 function in the same manner.

Figure 5:
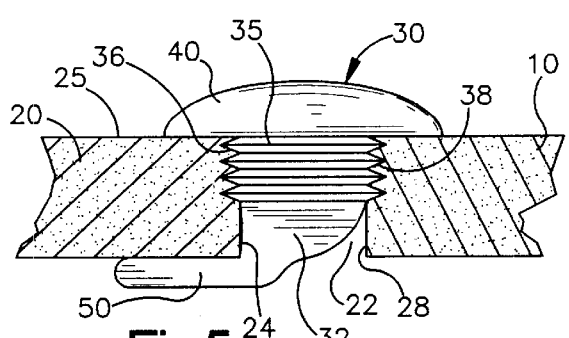
FIG. 5 is a sectional view taken along line 5—5 in FIG. 1.

When the cranial flap 20 is placed into the opening in the skull 10, the second surface portion 38 on the main body portion 32 of the attachment device 30 engages a second kerf edge 28 on the skull 10 (see FIG. 5). The cranial flap 20 is then pressed into the opening in the skull until the cranial flap becomes flush with the skull. As the cranial flap 20 is pressed into the flush position illustrated in FIG. 5, the teeth 35 on the first surface portion 36 of the attachment device 30 grip the first kerf edge 24 on the cranial flap 20. Simultaneously, the teeth 35 on the second surface portion 38 of the attachment device 30 grip the second kerf edge 28 on the cranial flap 20. Frictional engagement between the first surface portion 36 and the first kerf edge 24 and between the second surface portion 38 and the second kerf edge 28 cause the cranial flap 20 to be wedged in the opening in the skull 10. This frictional engagement secures the cranial flap 20 to the skull 10.

The method and apparatus disclosed above has several advantages. The method and apparatus saves valuable time during surgery. Screws and plates, known in the art, are not required. The bioabsorbable material of the attachment devices 30, 130, and 230 do not show up permanently in CT scans. Finally, the attachment devices 30, 130 and 230 leave no permanent unsightly bumps under the patient's skin.

From the above description of the invention, those skilled in the art will perceive improvements, changes and modifications. For example, it will be apparent to those skilled in the art that a bioabsorbable screw or tack of some kind may be used to further secure the head portion of the attachment devices disclosed herein to the either the cranial flap or the skull. Such improvements, changes and modifications within the skill of the art are intended to be covered by the appended claims.

Having described the invention, we claim:

1. An apparatus for attaching a cranial flap to a skull during surgery, the cranial flap and the skull being spaced apart by a kerf defined by a first kerf edge on the cranial flap and a second kerf edge on the skull, said apparatus comprising:

at least one attachment device made of a bioabsorbable polymeric material, said at least one attachment device having a head portion, a main body portion, and an end portion that is deformable upon heating to a predetermined temperature;

said end portion of said at least one attachment device having a first condition in which said end portion extends axially from said main body portion and a second condition in which said end portion extends radially from said main body portion for engaging an inner surface of the cranial flap, said end portion being deformable from said first condition to said second condition during surgery by heating said end portion and forming said end portion around the first kerf edge of the cranial flap to clamp said at least one attachment device to the cranial flap;

said main body portion of said at least one attachment device including a first surface portion for attaching to the first kerf edge on the cranial flap and a second surface portion for attaching to the second kerf edge on the skull;

said at least one attachment device being positionable in the kerf between the cranial flap and the skull to secure the cranial flap to the skull by frictional engagement between said first surface portion against the first kerf edge and frictional engagement between said second surface portion against the second kerf edge;

said first surface portion on said main body portion of said at least one attachment device including teeth for engaging the first kerf edge on the cranial flap.

2. The apparatus of claim 1 wherein said second surface portion on said main body portion of said at least one attachment device includes teeth for engaging the second kerf edge on the skull.

3. The apparatus of claim 1 wherein said main body portion of said at least one attachment device is cylindrical.

4. The apparatus of claim 3 wherein said first and second surface portions said main body portion of said at least one attachment device comprise arcuate segments.

5. The apparatus of claim 1 wherein said main body portion of said at least one attachment device is rectangular.

6. The apparatus of claim 1 wherein said end portion of said at least one attachment device includes relief slots to aid in bending of said end portion in a lateral direction.

7. The apparatus of claim 6 wherein said head portion of said at least one attachment device includes relief slots to aid in bending of said end portion in a lateral direction.

8. The apparatus of claim 1 further comprising a plurality of attachment devices that are positionable around the periphery of the cranial flap.

9. The apparatus of claim 1 wherein said bioabsorbable polymeric material comprises polylactide (PLA).

10. The apparatus of claim 1 wherein said bioabsorbable polymeric material comprises polyglycolide (PGA).

11. The apparatus of claim 1 wherein said bioabsorbable polymeric material comprises a co-polymer of polylactide (PLA) and polyglycolide (PGA).

12. A method for re-attaching a cranial flap to a skull during surgery, said method comprising the steps of:

providing an attachment device made of a bioabsorbable material that is formable upon heating to a predetermined temperature, the attachment device having a head portion, a main body portion, and a deformable end portion extending axially from the main body portion;

placing the attachment device adjacent the cranial flap so that the head portion engages an outer surface of the cranial flap and the main body portion engages a first kerf edge of the cranial flap;

heating the end portion of the attachment device to a predetermined temperature;

bending the end portion of the attachment device around the cranial flap so that the end portion extends radially and engages an inner surface of the cranial flap; and pressing the cranial flap into an opening in the skull created by the removal of the cranial flap so that frictional engagement between the main body portion of the attachment device and the cranial flap and frictional engagement between the main body portion of the attachment device secures the cranial flap to the skull.

13. The method of claim 12 further comprising the step of cooling the end portion so that the attachment device becomes clampingly secured to the cranial flap.

14. The method of claim 12 further comprising the steps of:

providing a plurality of attachment devices;

placing the plurality of attachment devices around the periphery of the cranial flap in a spaced apart manner;

heating the end portion of each of the plurality of attachment devices; and bending the end portion of each of the plurality of attachment devices around the cranial flap to secure each of the plurality of attachment devices to the cranial flap.

15. The method of claim 12 wherein said bioabsorbable polymeric material comprises polylactide (PLA).

16. The method of claim 12 wherein said bioabsorbable polymeric material comprises polyglycolide (PGA).

17. The method of claim 12 wherein said bioabsorbable polymeric material comprises a co-polymer of polylactide (PLA) and polyglycolide (PGA).

* * * * *